(12) United States Patent
Imai

(10) Patent No.: US 7,706,498 B2
(45) Date of Patent: Apr. 27, 2010

(54) X-RAY CT APPARATUS

(75) Inventor: Yasuhiro Imai, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 12/100,235

(22) Filed: Apr. 9, 2008

(65) Prior Publication Data

US 2008/0253505 A1  Oct. 16, 2008

(30) Foreign Application Priority Data

Apr. 12, 2007  (JP)  ............................. 2007-104825

(51) Int. Cl.
*G01N 23/00* (2006.01)
*G01N 23/083* (2006.01)
(52) U.S. Cl. .............................. 378/8; 378/20; 378/95
(58) Field of Classification Search ............... 378/4–20, 378/62, 63, 95, 210; 600/413, 425, 428, 600/481, 502, 509; 382/130
See application file for complete search history.

(56) References Cited

U.S. PATENT DOCUMENTS

| | | | |
|---|---|---|---|
| 3,954,098 A | | 5/1976 | Dick et al. |
| 4,446,873 A | | 5/1984 | Groch et al. |
| 4,547,892 A | * | 10/1985 | Richey et al. .................. 378/8 |
| 5,832,051 A | * | 11/1998 | Lutz ............................ 378/8 |
| 6,185,271 B1 | * | 2/2001 | Kinsinger .................... 378/19 |
| 6,233,478 B1 | * | 5/2001 | Liu ............................ 600/428 |
| 6,275,560 B1 | * | 8/2001 | Blake et al. .................... 378/8 |
| 6,470,208 B1 | * | 10/2002 | Woodford et al. ........... 600/428 |
| 6,504,894 B2 | | 1/2003 | Pan et al. |
| 6,628,981 B2 | * | 9/2003 | Baker et al. .................. 600/425 |
| 6,708,052 B1 | * | 3/2004 | Mao et al. .................... 600/407 |
| 6,865,248 B1 | | 3/2005 | Rasche et al. |
| 7,020,511 B2 | * | 3/2006 | Boyd et al. .................. 600/428 |
| 7,236,559 B2 | * | 6/2007 | Jha et al. ....................... 378/5 |
| 7,251,308 B2 | | 7/2007 | Tsuyuki |
| 7,522,696 B2 | | 4/2009 | Imai |
| 7,542,544 B2 | * | 6/2009 | Rubin et al. .................. 378/62 |
| 2004/0077941 A1 | | 4/2004 | Reddy et al. |
| 2005/0058248 A1 | * | 3/2005 | Klingenbeck-Regn ....... 378/95 |
| 2006/0140337 A1 | * | 6/2006 | Miyazaki et al. .............. 378/8 |

FOREIGN PATENT DOCUMENTS

| | | |
|---|---|---|
| JP | 2003-164446 | 6/2003 |
| JP | 2006-105749 | 4/2006 |

* cited by examiner

*Primary Examiner*—Edward J Glick
*Assistant Examiner*—Anastasia Midkiff
(74) *Attorney, Agent, or Firm*—Armstrong Teasdale LLP

(57) ABSTRACT

For the purpose of X-ray CT imaging a heart of a subject with high image quality while reducing stress on the subject, once an optimal cardiac phase has been set by an optimal cardiac phase setting section 30*b* and a target position in a subject to be scanned when the cardiac phase of the subject is at an optimal cardiac phase is defined at a target position defining section 30*c*, a transport-starting-cardiac-phase calculating section 30*b* calculates a transport-starting cardiac phase such that the target position is scanned at the optimal cardiac phase, using the optimal cardiac cycle, target position, scan start position, transport speed of an imaging table, and approach-run time for the imaging table. A scan control section starts transport at the imaging table 4 when the cardiac phase of the subject coincides with the transport-starting cardiac phase, and performs a helical scan with a helical pitch of one or more, for example.

17 Claims, 9 Drawing Sheets

X-RAY CT APPARATUS

CROSS REFERENCE TO RELATED APPLICATIONS

This application claims the benefit of Japanese Patent Application No. 2007-104825 filed Apr. 12, 2007, which is hereby incorporated by reference in its entirety.

BACKGROUND OF THE INVENTION

The subject matter disclosed herein relates to an X-ray CT (Computed Tomography) apparatus for imaging a subject by helical scanning.

Conventionally, X-ray CT imaging on a heart, especially, coronary arteries or the like, of a subject to be imaged involves so-called electrocardiographic gating imaging in which imaging is performed in synchronization with heartbeats.

The electrocardiographic gating imaging includes a prospective imaging method and a retrospective imaging method. The prospective imaging method comprises observing a cardiac cycle averaged based on a plurality of latest heartbeats, and collecting projection data for image reconstruction in synchronization with a cardiac phase at which motion of the heart is considered to be slowest, for example, at a 75% phase of the averaged cardiac cycle (see Japanese Patent Application Laid Open No. 2006-006531, for example). The retrospective imaging method comprises imaging a subject by a helical scan with a relatively small helical pitch, for example, with a pitch of the order of 0.2, while monitoring electrocardiographic signals from the subject, to collect the electrocardiographic signals for the subject and projection data for the subject simultaneously, and later extracting only projection data corresponding to an arbitrary cardiac phase for image reconstruction (see Japanese Patent Application Laid Open No. 2003-164446, for example).

Another method for reconstructing a tomographic image of coronary arteries or the like in a heart is known as a so-called multi-segment image reconstruction method. The method comprises collecting projection data in a plurality of segments at the same cardiac phase over several heartbeats, or extracting such projection data from those continuously collected in a helical scan, combining the projection data over view angles required in reconstruction of an image for one slice, and reconstructing a tomographic image. In general, reconstruction of an image for one slice requires projection data over a view angle of at least an X-ray beam fan angle plus 180°, and in a case that projection data collected during one rotation of a gantry cannot cover the view angle, a tomographic image for one slice can be reconstructed using the multi-segment image reconstruction method by combining segmented projection data collected in a period of time corresponding to a plurality of consecutive heartbeats.

Such electrocardiographic gating imaging or multi-segment image reconstruction enables image reconstruction processing to be achieved using projection data corresponding to a given cardiac phase zone in which motion of the heart is slow, so that a tomographic image of a heart in which blurring of a subject due to cardiac motion is suppressed can be obtained.

SUMMARY OF THE INVENTION

In recent years, advances have been made for an X-ray detecting section, such as an increase in the number of detector rows, expansion in the width in a slice direction, and improvement in the gantry rotation speed; however, since the width of the X-ray detecting section in the slice direction still remains shorter than the length of the heart, the whole heart cannot be imaged without shifting the imaged position in an axial or cine scan. Hence, the aforementioned prospective imaging method generally requires the imaged position to be shifted a plurality of number of times, thus inhibiting high-speed imaging and leading to a long constraining time for the subject. On the other hand, the retrospective imaging method requires a continuous exposure of the subject to X-rays over a long period of time, resulting in a high exposure dose to the subject.

Especially when such electrocardiographic gating imaging is combined with contrast imaging, the total amount of a contrast agent is increased because of relatively quick flow of the contrast agent injected into the subject, further increasing stress on the subject.

Moreover, when a tomographic image is obtained through multi-segment image reconstruction, discontinuity between projection data segments results in a problem of generation of artifacts in a tomographic image.

The present invention has been made in view of such circumstances, and its object is to provide an X-ray CT apparatus capable of imaging a heart of a subject with high image quality while reducing stress on the subject.

In its first aspect, the present invention provides an X-ray CT apparatus comprising: an X-ray data collecting system provided with an X-ray generating section for generating X-rays and an X-ray detecting section comprising a multiplicity of X-ray detector elements two-dimensionally arranged, facing each other across a cavity and provided rotatably around a given axis; an imaging table for carrying said subject placed thereon through said cavity along said given axis; scan control device for controlling said X-ray data collecting system and said imaging table to perform a helical scan on said subject to thereby collect projection data; and image reconstructing device for performing image reconstruction processing based on said collected projection data to produce a tomographic image of said subject, said apparatus further comprising: cardiac motion identifying device for identifying cardiac motion of said subject; optimal cardiac phase setting device for setting an optimal cardiac phase for said subject; target position defining device for defining a target position to be scanned in a direction along said given axis of said subject when a cardiac phase for said subject is at said optimal cardiac phase; and transport-starting-cardiac-phase calculating device for calculating a transport-starting cardiac phase corresponding to a time at which transport of said imaging table is to be started such that said target position is scanned at said optimal cardiac phase, using a cardiac cycle of said subject determined based on said identified cardiac motion, a scan start position in said subject, a transport speed of said imaging table, and an approach-run time for said imaging table, wherein said scan control device controls said imaging table to start transport of said imaging table when the cardiac phase of said subject determined based on said identified cardiac motion coincides with said calculated transport-starting cardiac phase.

In its second aspect, the present invention provides the X-ray CT apparatus of the first aspect, wherein: said transport-starting-cardiac-phase calculating device calculates said transport-starting cardiac phase according to the following equation:

$$Stph = Tgph - ((((Pm-Ps)/Vt+Tr)/Th) \times 100),$$

where Stph denotes said transport-starting cardiac phase, Tgph denotes said optimal cardiac phase, Pm denotes said target position, Ps denotes said scan start position, Vt denotes said transport speed, Tr denotes said approach-run time, and Th denotes said cardiac cycle.

In its third aspect, the present invention provides the X-ray CT apparatus of the first or second aspect, wherein: said scan control device controls said X-ray data collecting system to abort X-ray generation by said X-ray generating section midway through said helical scan when a difference between the cardiac cycle based on cardiac motion identified by said cardiac motion identifying device before said helical scan and the cardiac cycle based on cardiac motion identified by said cardiac motion identifying device during said helical scan is equal to or greater than a given period of time.

In its fourth aspect, the present invention provides the X-ray CT apparatus of the first or second aspect, wherein: said scan control device makes control to generate warning when the difference between the cardiac cycle based on cardiac motion identified by said cardiac motion identifying device before said helical scan and the cardiac cycle based on cardiac motion identified by said cardiac motion identifying device during said helical scan is equal to or greater than a given period of time.

In its fifth aspect, the present invention provides the X-ray CT apparatus of the first or second aspect, wherein: said scan control device controls said X-ray data collecting system and said imaging table to perform a second helical scan in synchronization with termination of said helical scan when the difference between the cardiac cycle based on cardiac motion identified by said cardiac motion identifying device before said helical scan and the cardiac cycle based on cardiac motion identified by said cardiac motion identifying device during said helical scan is equal to or greater than a given period of time.

In its sixth aspect, the present invention provides the X-ray CT apparatus of the fifth aspect, wherein: said scan control device controls said X-ray data collecting system and said imaging table to perform said second helical scan with a reversed direction of transport of said imaging table.

In its seventh aspect, the present invention provides the X-ray CT apparatus of any one of the first—sixth aspects, wherein: said scan control device controls said X-ray data collecting system and said imaging table to perform a helical scan with a helical pitch of one or more.

In its eighth aspect, the present invention provides the X-ray CT apparatus of any one of the first—seventh aspects, wherein: said scan control device controls said X-ray data collecting system and said imaging table to perform a helical scan at a cycle of rotation of said X-ray data collecting system of 0.4 seconds or less.

In its ninth aspect, the present invention provides the X-ray CT apparatus of any one of the first—eighth aspects, further comprising: contrast injector device for injecting a contrast agent into said subject; and a transport-holding-time calculating device for calculating a transport holding time that should be kept from the start of injection of said contrast agent to the start of transport of said imaging table, using an approach-run time for said imaging table and a contrast delivery time representing a time required from injection of said contrast agent to arrival of said contrast agent at an imaged area, wherein said scan control device controls said contrast injector device to inject said contrast agent into said subject, and controls said imaging table to start transport of said imaging table after at least said transport holding time has passed.

In its tenth aspect, the present invention provides the X-ray CT apparatus of the ninth aspect, wherein: said transport-holding-time calculating device calculates said transport holding time according to the following equation:

$$Tw = Tz - Tr,$$

where Tw denotes said transport holding time, Tz denotes said contrast delivery time, and Tr denotes said approach-run time.

In its eleventh aspect, the present invention provides the X-ray CT apparatus of any one of the first—tenth aspects, wherein: said optimal cardiac phase setting device sets said optimal cardiac phase within 70-80%, where a phase covering a range from the peak of a first R-wave to the peak of a second R-wave subsequent to said first R-wave in a heartbeat waveform is represented as 0-100%.

In its twelfth aspect, the present invention provides the X-ray CT apparatus of any one of the first—eleventh aspects, wherein: said scan control device controls said X-ray data collecting system and said imaging table to perform scout imaging on said subject before said helical scan, and said target position defining device defines said target position on an image of said subject acquired in said scout imaging.

In its thirteenth aspect, the present invention provides the X-ray CT apparatus of any one of the first—eleventh aspects, wherein: said scan control device controls said X-ray data collecting system and said imaging table to perform a preliminary helical scan on said subject before said helical scan, and said target position defining device defines said target position on an image of said subject acquired in said preliminary helical scan.

In its fourteenth aspect, the present invention provides the X-ray CT apparatus of the twelfth or thirteenth aspect, further comprising: coronary artery detecting device for detecting an image representing a coronary artery of said subject by analyzing an image of said subject, wherein said target position defining device defines said target position at the position of the image representing said detected coronary artery.

In its fifteenth aspect, the present invention provides the X-ray CT apparatus of the fourteenth aspect, wherein: said coronary artery is a right coronary artery #2.

In its sixteenth aspect, the present invention provides the X-ray CT apparatus of any one of the first—fifteenth aspects, wherein: said cardiac motion identifying device identifies cardiac motion based on signals acquired by a cardiograph.

In its seventeenth aspect, the present invention provides the X-ray CT apparatus of any one of the first—fifteenth aspects, wherein: said cardiac motion identifying device identifies cardiac motion based on signals acquired by a pulsemeter.

As used herein, the "cardiac motion identifying device" may be, for example, device of identifying cardiac motion by detecting periodical body motion or heartbeat signals, constituted by electromagnetic waves or the like, synchronizing with cardiac motion of a subject, or device of identifying cardiac motion by receiving heartbeat signals detected by cardiac motion detecting device comprised of a cardiograph, pulsemeter or the like.

As used herein, the "cardiac cycle determined based on the identified cardiac motion" may be the time between two consecutive heartbeat signals, or the time obtained by calculating a time between two consecutive heartbeat signals in three or more consecutive heartbeat signals for each combination of the two consecutive heartbeat signals therein, and averaging the times between the heartbeat signals in such combinations. In the latter case, and in a case that the time between the heartbeat signals represents an extremely long or short cardiac cycle as compared with the previously acquired cardiac cycle, the time between those heartbeat signals is desirably unused in calculating a cardiac cycle. Thus, even if the heartbeat becomes out of order due to, for example, arrhythmia of the subject, the calculated cardiac cycle can be prevented from extreme variation, thus enabling approximation of a more substantial cardiac cycle by the calculated cardiac cycle. Moreover, the "cardiac cycle" may be represented by a time obtained by counting the number of heartbeat signals within a given period of time, and dividing the given period of time by the counted number of heartbeat signals.

As used herein, the term "position" in the "target position" or "scan start position" refers to a reference position of a scanned range, and may be considered as, for example, a position along said given axis based on a plane containing a straight line connecting an X-ray generation point (X-ray focus in an X-ray tube) in the X-ray generating section with a center of an X-ray detecting surface in the X-ray detecting section.

As used herein, the term "scan" refers to collection of projection data that can be used in reconstruction of a tomographic image by generating X-rays in the X-ray generating section and detecting X-rays passing through the imaging space in the cavity by the X-ray detecting section while rotating the X-ray data collecting system.

As used herein, the term "helical pitch" refers to a ratio of a travel distance of the imaging table per rotation of the X-ray data collecting system to the width of the X-ray detecting surface in the X-ray detecting section in the slice direction. A practical helical pitch that may be contemplated is in a range of 0.2-3.0.

As used herein, by the phrase "at a cycle of rotation of the X-ray data collecting system of 0.4 seconds or less" is meant that the rotation speed of the X-ray data collecting system is set to such a value as to result in a cycle of rotation of 0.4 seconds or faster. A practical cycle of rotation that may be contemplated is in a range of 0.1-0.4 seconds.

As used herein, the term "approach-run time for the imaging table" refers to a time required in an approach run needed to activate the stopping imaging table to move at a given speed.

The "subject" may include animal patients in addition to human patients.

According to the X-ray CT apparatus of the present invention, once an optimal cardiac phase has been set by the optimal cardiac phase setting device and a target position in a subject is defined by the target position defining device, the transport-starting-cardiac-phase calculating device calculates a transport-starting cardiac phase such that the aforementioned target position is scanned at the aforementioned optimal cardiac phase, using a cardiac cycle of the subject, a scan start position in the subject, a transport speed of the imaging table, and an approach-run time for the imaging table, and the scan control device starts transport of the imaging table for a helical scan on the subject when the cardiac phase of the subject coincides with the transport-starting cardiac phase. Therefore, imaging can be made on a region to be imaged in the subject at a high speed and with a low X-ray dose such that a desired portion in the subject, for example, a portion having significant variation due to heartbeats, can be scanned at a desired cardiac phase, for example, at a phase at which the variation due to heartbeats is slowest, and thus, a heart of a subject can be imaged with high image quality while reducing stress on the subject.

DETAILED DESCRIPTION OF THE INVENTION

Now embodiments of the present invention will be described with reference to the accompanying drawings.

An X-ray CT apparatus in accordance with one embodiment of the present invention will be described.

Figure 1:
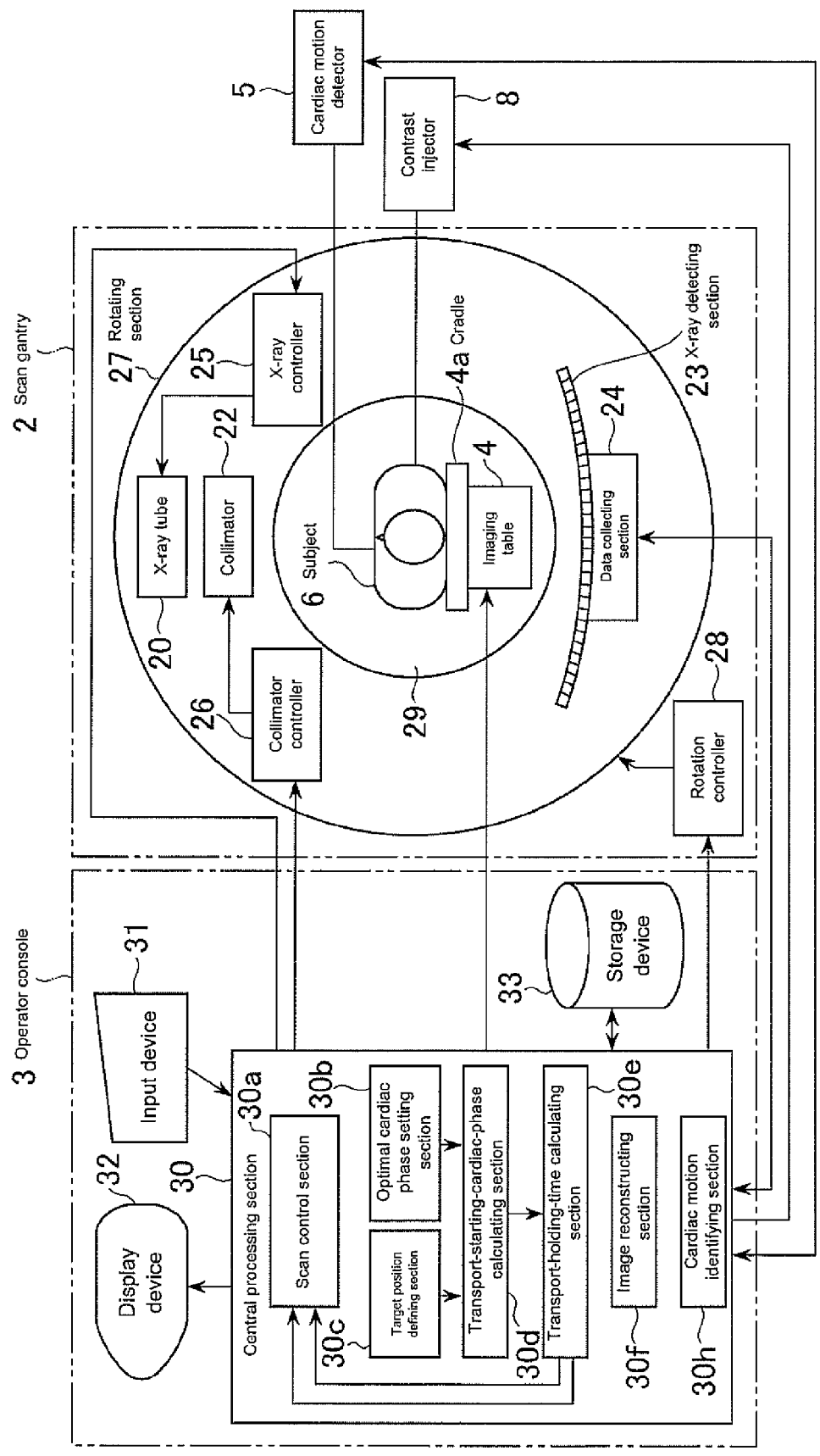
FIG. 1 is a diagram showing a configuration of an X-ray CT apparatus in accordance with one embodiment of the present invention.

FIG. 1 is a block diagram showing an overall configuration of an X-ray CT apparatus 1 of the present embodiment. As shown in FIG. 1, the X-ray CT apparatus 1 of the present embodiment comprises a scan gantry 2, an operator console 3, an imaging table 4, a cardiac motion detector 5, and a contrast injector 8.

The scan gantry 2 comprises an X-ray tube 20, a collimator 22, an X-ray detecting section 23, a data collecting section 24, an X-ray controller 25, a collimator controller 26, a rotating section 27, and a rotation controller 28. The scan gantry 2 has therein a bore 29 through which a cradle 4a of the imaging table 4 for placing thereon the subject 6 is transported, and the X-ray tube 20 and X-ray detecting section 23 are disposed to face each other across the bore 29.

The X-ray tube 20 is provided for emitting X-rays. In the present embodiment, the X-ray tube 20 generates X-rays based on a control signal from the X-ray controller 25 to emit X-rays toward the subject 6 carried into the bore 29.

The collimator 22 is disposed between the X-ray tube 20 and X-ray detecting section 23. The collimator 22 is made from, for example, two plates provided in a channel direction x and two plates provided in a slice direction z. The collimator 22 moves the two plates provided in each direction independently based on a control signal from the collimator controller 26 to intercept the X-rays emitted from the X-ray tube 20 in that direction to form them into a cone-like shape, thus regulating the coverage of X-ray emission.

The X-ray detecting section 23 is disposed to face the X-ray tube 20 across the bore 29. The X-ray detecting section 23 detects X-rays emitted by the X-ray tube 20 in a plurality of view directions around the subject 6 and passing through the subject 6 to generate projection data for each view direction.

Figure 2:
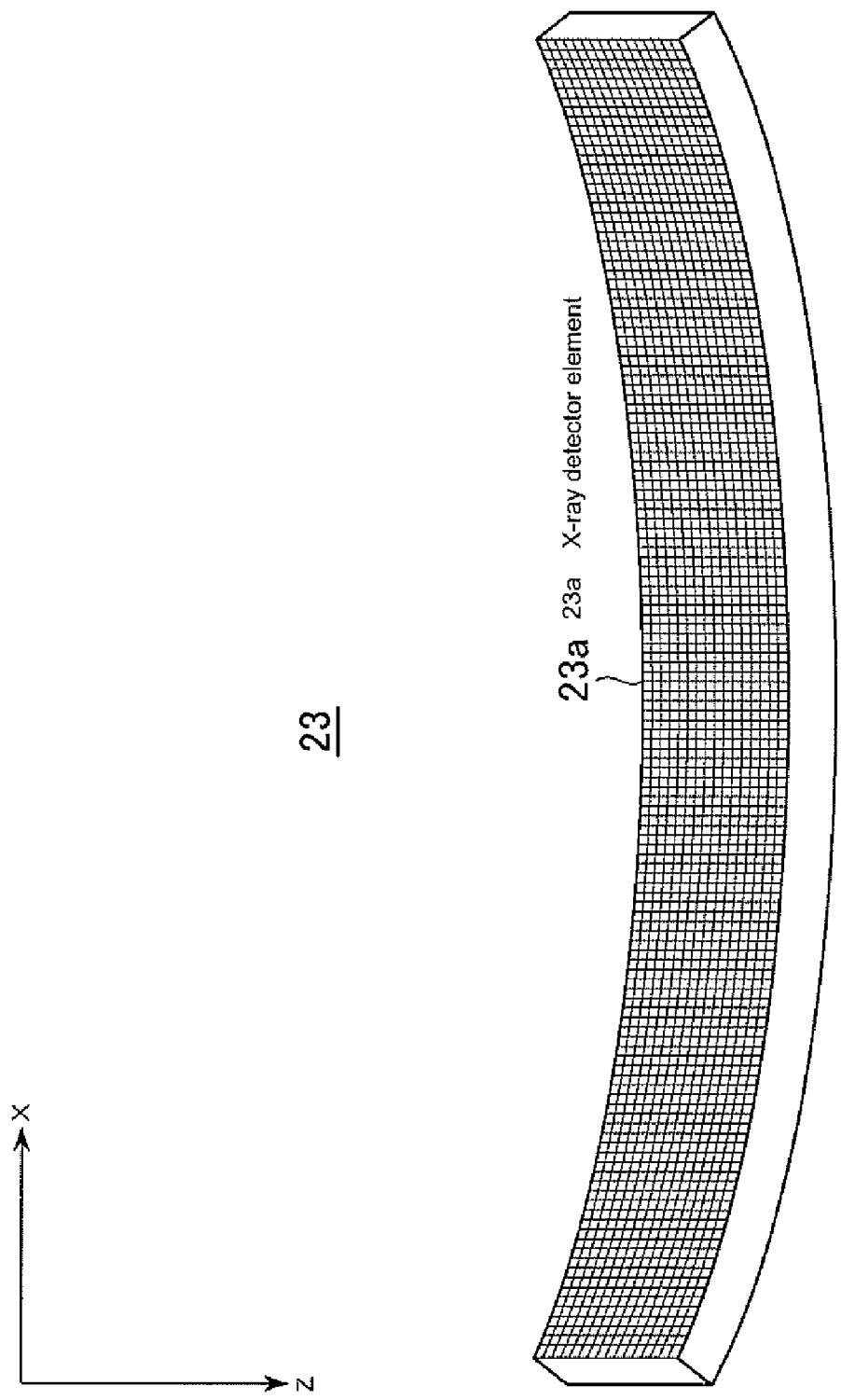
FIG. 2 is a diagram showing a configuration of an X-ray detecting section in accordance with one embodiment of the present invention.

FIG. 2 is a perspective view showing a configuration of the X-ray detecting section 23. As shown in FIG. 2, the X-ray detecting section 23 has a multiplicity of X-ray detector elements 23a two-dimensionally arranged in an array in the channel direction x and slice direction z. Specifically, the X-ray detecting section 23 has the detector elements 23a two-dimensionally arranged in an array in the channel direction x and slice direction z, the channel direction x being along a rotation angle direction for the X-ray tube 20 rotated by the rotating section 27 around a body axis direction of the subject 6, and the slice thickness direction z being a direction generally perpendicular to a plane formed by a trajectory drawn by the rotation of the X-ray tube 20 by the rotating section 27. The two-dimensionally arranged plurality of X-ray detector elements 23a together form a plane of X-ray impingement curved in the form of a cylindrical concave surface. In such a configuration, 1,000 X-ray detector elements 23a, for example, are arranged in the channel direction x, and eight X-ray detector elements 23a, for example, are arranged in the slice direction z. While the X-ray detecting section 23 desirably is such a multi-row X-ray detector or X-ray area detector in a matrix structure, it may be a single-row X-ray detector.

The detector elements 23a comprise a scintillator (not shown), for example, for converting the detected X-rays into light, and photodiodes (not shown) for converting the light converted by the scintillator into an electrical charge, so that the X-ray detecting section 23 is constructed as a solid state detector. It should be noted that the detector elements 23a are not limited thereto, and may be, for example, semiconductor detector elements employing cadmium-tellurium (CdTe), or of an ionization-chamber type using a xenon (Xe) gas.

Figure 3:
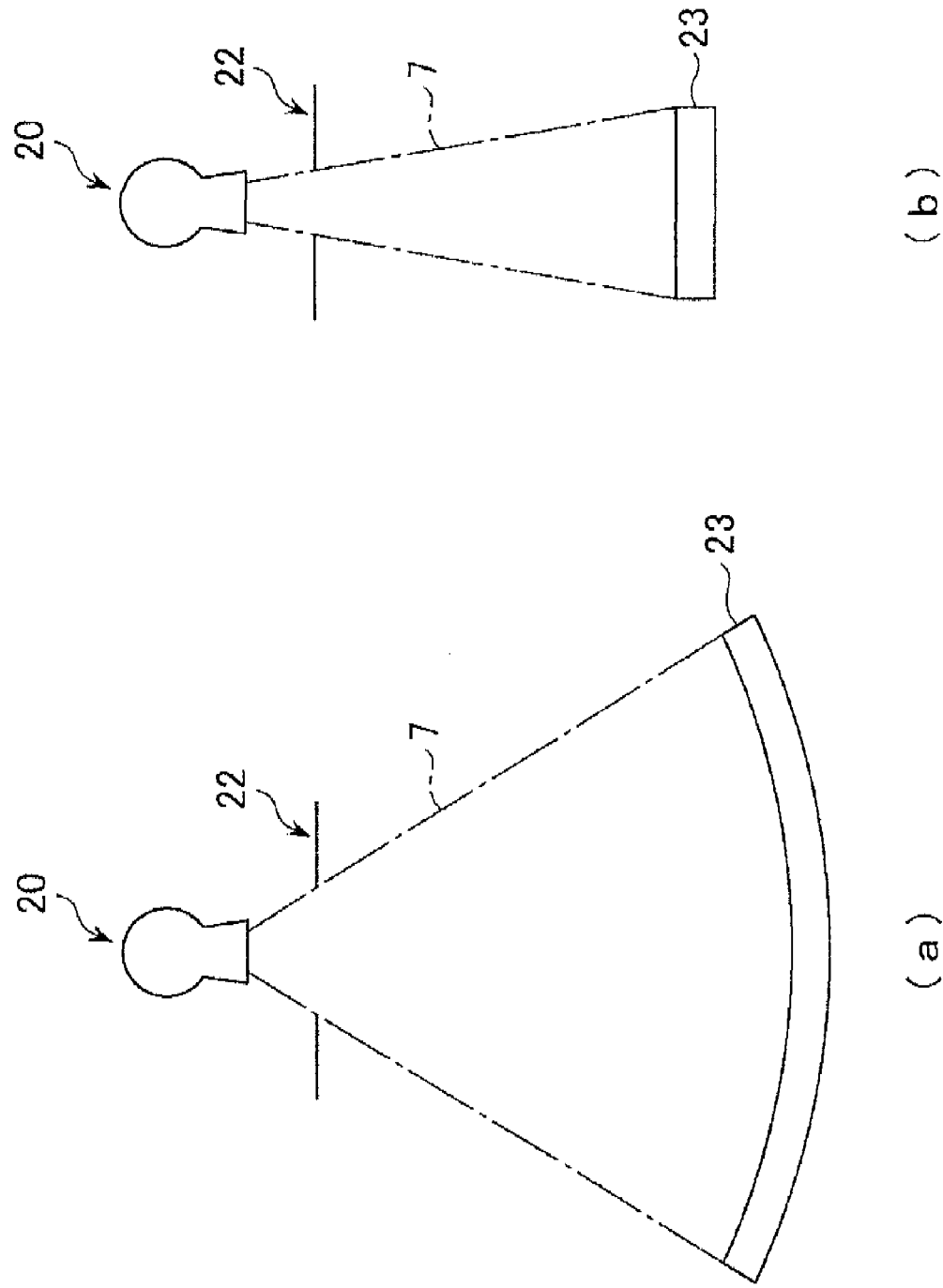
FIGS. 3(a) and 3(b) are diagrams showing a mutual relationship among an X-ray tube, a collimator, and an X-ray detecting section in accordance with one embodiment of the present invention.

FIGS. 3(a) and 3(b) are diagrams showing the mutual relationship among the X-ray tube 20, collimator 22 and X-ray detecting section 23. In FIG. 3, (a) is a diagram as viewed in the slice direction z, and (b) is a diagram as viewed in the channel direction x.

As shown in FIGS. 3(a) and (b), the X-rays 7 emitted from the X-ray tube 20 are formed into a cone-like shape by the collimator 22, and cast onto the X-ray detecting section 23. In imaging the subject 6, the subject 6 is laid on the imaging table 4, and the subject 6 thus laid is carried into the bore 29. The X-rays 7 are then emitted in a plurality of view directions from the circumference around the subject 6 around the slice direction z of the subject 6, and X-rays passing through the subject 6 through the collimator 22 are detected by the X-ray detecting section 23 for each view direction to generate projection data for the subject 6.

The data collecting section 24 collects the projection data detected and generated by the X-ray detecting section 23, and outputs them to the operator console 3. The data collecting section 24 comprises, for example, a selection/addition switching circuit (not shown), and an analog-to-digital converter (not shown). In response to a control signal from the operator console 3, the selection/addition switching circuit selects projection data and adds them in a varying combination, and outputs the resulting data to the analog-to-digital converter. The projection data selected or added in a varying combination by the selection/addition switching circuit are converted from an analog signal to a digital signal by the analog-to-digital converter and output to the operator console 3.

The X-ray controller 25 outputs a control signal to the X-ray tube 20 to control the X-ray tube 20, in response to a control signal from the operator console 3. The X-ray controller 25 also outputs a control signal to make control so that the center of emission from the X-ray tube 20 is moved in the slice direction z, in response to a control signal from the operator console 3.

The collimator controller 26 outputs a control signal to the collimator 22 for controlling the collimator 22 to shape X-rays emitted from the X-ray tube 20, in response to a control signal from the operator console 3.

The rotating section 27 rotates around an iso-center of the bore 29 in response to a control signal from the rotation controller 28. The rotating section 27 is provided with the X-ray tube 20, collimator 22, X-ray detecting section 23, data collecting section 24, X-ray controller 25, and collimator controller 26, which are changed in position relative to the subject 6 carried into the bore 29 with rotation of the rotating section 27. By rotating the rotating section 27, X-rays are emitted in a plurality of view directions around the slice direction z of the subject 6, and X-rays passing through the subject are detected.

The rotation controller 28 outputs a control signal to the rotating section 27 for controlling the rotating section 27 to rotate, in response to a control signal from the operator console 3.

The imaging table 4 transports the cradle 4a for laying thereon the subject 6 along the body axis of the subject 6, i.e., along a z-axis, into the bore 29 in the scan gantry 2. The imaging table 4 controls the position of the cradle 4a based on a control signal from the operator console 3. The imaging table 4 also changes a scanned position by moving the cradle 4a for laying thereon the subject 6, as needed.

The cardiac motion detector 5 is for detecting cardiac motion of the subject 6. The cardiac motion detector 5 is comprised of, for example, a cardiograph to detect heartbeat signals from the subject 6 to generate electrocardiographic signals, and calculates a cardiac cycle based on the latest and adjacent electrocardiographic waveforms etc. at the same phase. The cardiac motion detector 5 is connected with the operator console 3, and outputs the generated electrocardiographic signals and calculated cardiac cycle to the operator console 3. The cardiac motion detector 5 may also be comprised of a pulsemeter for detecting pulses.

The contrast injector 8 is for injecting a contrast agent into the subject 6. The contrast injector 8 is connected with the operator console 3, and controls injection of the contrast agent into the subject 6 according to a control signal from the operator console 3.

The operator console 3 comprises a central processing apparatus 30, an input device 31, a display device 32, and a storage device 33.

The central processing apparatus 30 is comprised of, for example, a computer, and has a scan control section 30a, an optimal cardiac phase setting section 30b, a target position defining section 30c, a transport-starting-cardiac-phase calculating section 30d, a transport-holding-time calculating section 30e, an image reconstructing section 30f, and a cardiac motion identifying section 30h.

The scan control section 30a controls the scan gantry 2 and imaging table 4 to perform a helical scan on the subject 6 to collect projection data. In the present embodiment, the scan control section 30a controls several sections to perform a scan based on scan conditions input via the input device 31, in which scan X-rays are emitted from the X-ray tube 20 toward the subject 6 and X-rays passing through the subject 6 are detected at the X-ray detecting section 23.

More particularly, the scan control section 30a outputs a control signal to the imaging table 4 based on the scan conditions to transport the imaging table 4 into/out of the bore 29 of the scan gantry 2 and regulate the position at which the subject 6 is scanned. The scan control section 30a also outputs a control signal to the rotation controller 28 to rotate the rotating section 27 of the scan gantry 2 and control a cycle of rotation of the rotating section 27. Moreover, the scan control section 30a outputs a control signal to the X-ray controller 25 to control the tube voltage for the X-ray tube 20 and the time at which X-rays are emitted. The scan control section 30a also outputs a control signal to the collimator controller 26 for controlling the collimator 22 to shape X-rays. Furthermore, the scan control section 30a outputs a control signal to the data collecting section 24 to control it to collect projection data acquired by the detector elements 23a in the X-ray detecting section 23.

The cardiac motion identifying section 30h acquires electrocardiographic signals or information on the cardiac cycle from the cardiac motion detector 5 to identify cardiac motion of the subject 6.

The optimal cardiac phase setting section 30b sets an optimal cardiac phase for the subject 6. Although the optimal cardiac phase setting section 30b sets the optimal cardiac phase according to an input operation by the operator, a given cardiac phase may be preset as optimal cardiac phase. The optimal cardiac phase setting section 30b also sets the optimal cardiac phase within 70-80%, where a phase covering a range from the peak of a first R-wave to the peak of a second R-wave subsequent to the first R-wave in a heartbeat waveform is represented as 0-100%. This setting is made because a cardiac phase at which motion of the heart is slowest lies near 75%, and a phase that is significantly deviated from an objective cardiac phase can thus be prevented from being set as optimal cardiac phase due to a mistake in an inputting operation, and in addition, the individual difference of the subject 6 can be absorbed.

The target position defining section 30c defines a target position to be scanned in the body axis direction of the subject 6, i.e., in the z-direction, when the cardiac phase of the subject 6 is at the aforementioned set optimal cardiac phase.

The transport-starting-cardiac-phase calculating section 30d calculates a transport-starting cardiac phase corresponding to a time at which transport of the cradle 4a is to be started such that the defined target position is scanned at the set optimal cardiac phase, using a cardiac cycle of the subject 6 determined based on the cardiac motion identified by the cardiac motion identifying section 30h, a scan start position in the subject 6, a transport speed of the cradle 4a, and an approach-run time for the cradle 4. The transport-starting-cardiac-phase calculating section 30d calculates the transport-starting cardiac phase according to the following equation, for example:

$$Stph=Tgph-((((Pm-Ps)/Vt+Tr)/Th)\times 100), \quad (1)$$

where Stph denotes the transport-starting cardiac phase, Tgph denotes the optimal cardiac phase, Pm denotes the target position, Ps denotes the scan start position, Vt denotes the transport speed, Tr denotes the approach-run time, and Th denotes the cardiac cycle.

The scan control section 30a controls the imaging table 4 to start transport of the cradle 4a when the cardiac phase of the subject 6 determined based on the cardiac motion identified by the cardiac motion identifying section 30h coincides with the calculated transport-starting cardiac phase Stph. The scan control section 30a also controls the scan gantry 2 and imaging table to perform a helical scan with a helical pitch of one or more after the transport speed of the imaging table 4 has become constant.

The transport-holding-time calculating section 30e calculates a transport holding time Tw that should be kept from the start of injection of the contrast agent to the start of transport of the cradle 4a, using an approach-run time Tr for the cradle 4 and a contrast delivery time Tz representing a time required from injection of the contrast agent to arrival of the contrast agent at an imaged area. The transport-holding-time calculating section 30e calculates the transport holding time Tw according to the following equation, for example:

$$Tw=Tz-Tr, \quad (2)$$

where Tw denotes the transport holding time, Tz denotes the contrast delivery time, and Tr denotes the approach-run time.

The scan control section 30a controls the contrast injector 8 to inject a contrast agent into the subject 6, and controls the imaging table 4 to start transport of the cradle 4a after at least the transport holding time Tw has passed.

The image reconstructing section 30f performs image reconstruction processing based on the collected projection data to produce a tomographic image of the subject 6. The image reconstructing section 30f applies interpolation processing using the collected projection data, and reconstructs the tomographic image of the subject 6 according to a known reconstruction technique such as, for example, a three-dimensional image reconstruction technique represented by a Feldkamp method, or a convolution backprojection technique. The image reconstructing section 30f is connected to the storage device 33 to store the produced tomographic image of the subject 6 in the storage device 33.

When the difference between the cardiac cycle based on cardiac motion identified before the helical scan and that based on cardiac motion identified during the helical scan is equal to or greater than a given period of time, for example, 0.2 seconds or more, the scan control section 30a assumes that some anomaly occurs in the cardiac cycle, and controls the scan gantry 2 and imaging table 4 to abort X-ray generation from the X-ray tube 20 midway through the helical scan, generate warning, and forcefully terminate the helical scan. The scan control section 30a then controls the scan gantry 2 and imaging table 4 to transport the cradle 4a to a given position to allow a second helical scan, and perform the second helical scan in synchronization with termination of the preceding helical scan. At that time, instead of moving the cradle 4a back to the initial position at one end of the imaging range in the body axis direction of the subject 6, the scan control section 30a moves the cradle 4a to a given position at the other end of the imaging range to perform the helical scan with a reversed direction of transport of the cradle 4a. That is, the second helical scan is performed with a reversed start and end points in the preceding helical scan. Thus, a time required to start the second helical scan can be reduced.

The scan control section 30a also controls the scan gantry 2 and imaging table 4 to perform a helical scan at a cycle of rotation of the rotating section 27 of 0.4 seconds or less. The reason of this is as follows: when general imaging conditions include a scan width (a width of an imaging range in the slice direction that can be scanned at a time without moving the scan position in the z-direction for image reconstruction) of 40 mm, a length of a heart of 120 mm, a helical pitch of one, and a cardiac cycle of 0.8 seconds, for example, imaging on the whole heart requires two rotations of the rotating section 27, and to complete such imaging within a time corresponding to one cardiac cycle, the cycle of rotation of the rotating section 27 should be 0.4 seconds or less. However, even when the cycle of rotation of the rotating section 27 is greater than 0.4 seconds, it is possible to image the whole heart within a time corresponding to one cardiac cycle with a helical pitch set to a value greater than one. It should be noted that these imaging conditions desirably be determined considering the cardiac cycle of the subject 6, upper limit of the cycle of rotation of the rotating section 27, upper limit of the transport speed of the cradle 4a, upper limit of the X-ray dose by the X-ray tube 20, desirable image quality for a tomographic image, and the like.

Moreover, the scan control section 30a controls the scan gantry 2 and imaging table 4 to perform scout imaging on the subject 6 before the helical scan, and the target position defining section 30c defines a target position on an image of the subject 6 acquired in the scout imaging. However, there may be a case that spatial resolution of the scout image acquired in scout imaging is too low to define an objective position, for example, a position on a coronary artery, as the target position. In such a case, the scan control section 30a controls the scan gantry 2 and imaging table 4 to perform a preliminary helical scan on the subject 6 with a lower X-ray dose than that in actual imaging before the helical scan, and the target position defining section 30c defines a target position on an image of the subject 6 acquired in the preliminary helical scan, for example, on an MPR image based on volume data or on a projection image obtained by projecting volume data onto a given plane.

The input device 31 is comprised of input devices such as, for example, a keyboard and a mouse. The input device 31 is provided for supplying to the central processing apparatus 30 several kinds of information such as, for example, imaging conditions including actual scan conditions, and information on the subject 6.

The display device 32 is comprised of, for example, a CRT (cathode ray tube). The display device 32 displays an enhanced image of the subject 6 produced by the image producing section 30e and several other kinds of information based on instructions from the central processing apparatus 30.

The storage device 33 is comprised of a memory for storing several kinds of data including images produced by the image producing section 30d, programs and the like. The storage device 33 is accessed by the central processing apparatus 30 for the stored data as needed.

It should be noted that the rotating section 27 is an example of the X-ray data collecting system in the present invention, and the bore 29 is an example of the cavity in the present invention.

Now an X-ray CT imaging method using the X-ray CT apparatus 1 in accordance with the present embodiment will be described. It should be noted that exemplary scan conditions here include a scan width of 40 mm, a rotation speed of the rotating section 27 in the scan gantry 2 of 0.35 seconds/rotation, and a helical pitch of 1.375.

Figure 4:
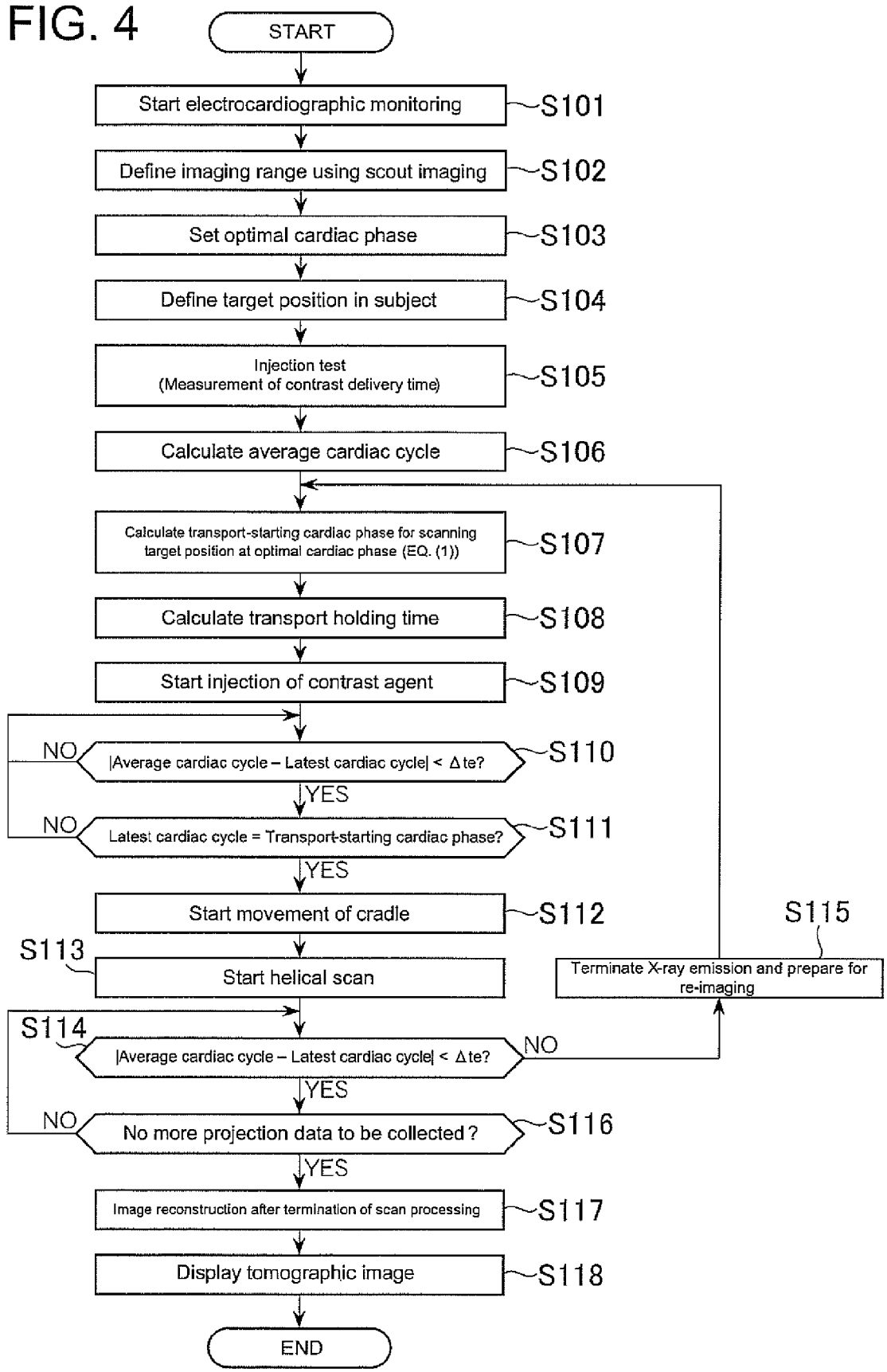
FIG. 4 is a flow chart showing an X-ray CT imaging method using the X-ray CT apparatus in accordance with one embodiment of the present invention.
Figure 5:
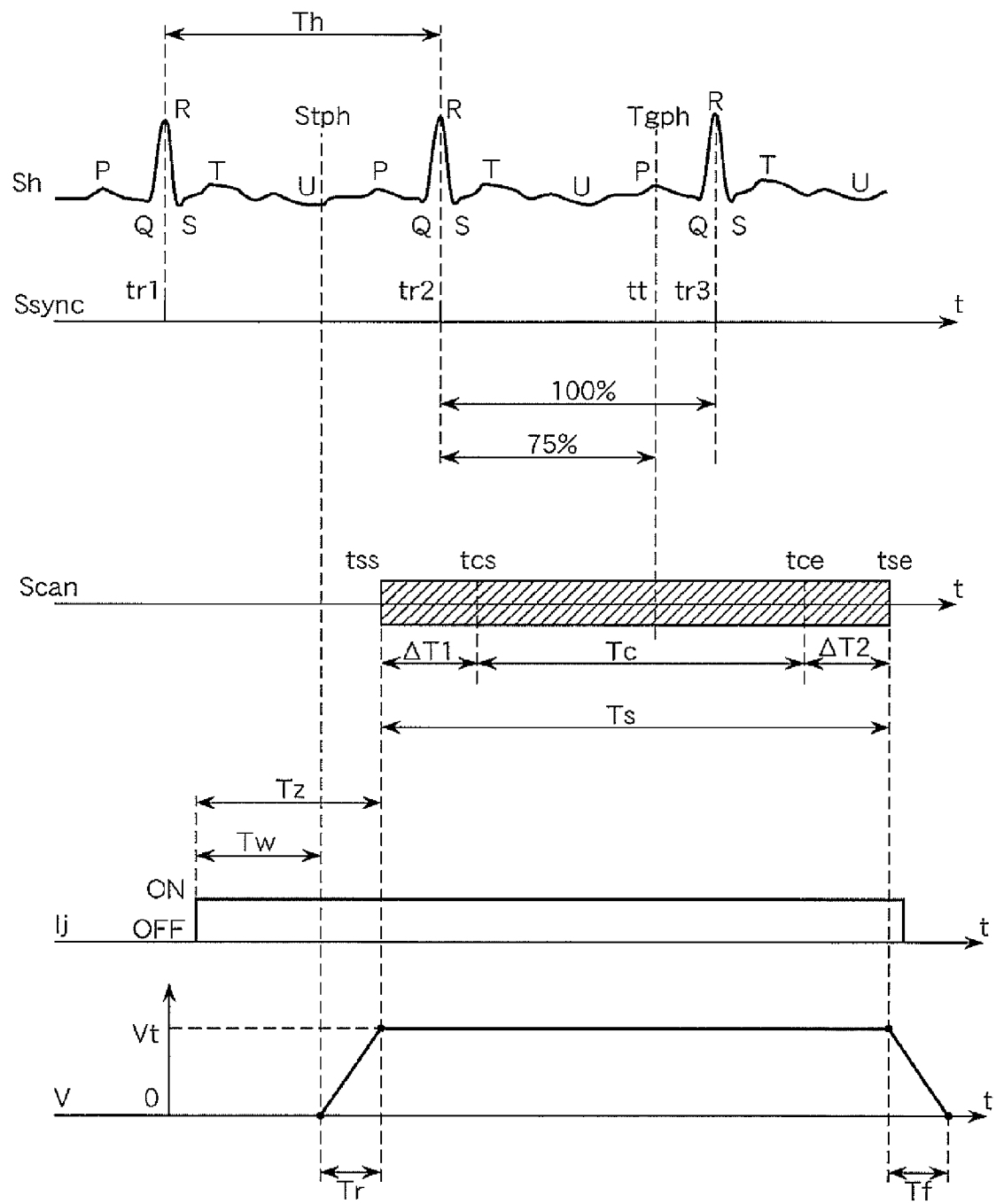
FIG. 5 is a diagram showing a time chart of scan processing in the X-ray CT apparatus in accordance with one embodiment of the present invention.

FIG. 4 is a flow chart showing an X-ray CT imaging method using the X-ray CT apparatus in accordance with the present embodiment. FIG. 5 shows a time chart of scan processing in accordance with the present embodiment. FIG. 5 shows an electrocardiographic signal Sh of the subject 6, an electrocardiographic gating signal Ssync, a projection data collection period Scan in a helical scan, a period Ij for injecting a contrast agent in the subject 6, and a transport speed V of the cradle 4a, with a horizontal axis of a time T. In the electrocardiographic signal Sh, peaks of waves P, Q, R, S, T, U in an electrocardiographic waveform are illustrated with these symbols. In the electrocardiographic gating signal Ssync, electrocardiographic gating signals that are consecutively detected are illustrated as tr1, tr2, . . . A cardiac phase is represented by a proportion (%) with respect to 100% representing a range from one R peak to a next R peak.

First, the subject 6 is placed on the cradle 4a in the imaging table 4 and is attached with the cardiac motion detector 5 comprised of a cardiograph, and monitoring of electrocardiographic signals is started (S101).

The scan control section 30a in the central processing apparatus 30 outputs a control signal to the scan gantry 2 and imaging table 4 to perform scout imaging by emitting X-rays onto the subject 6 while transporting the cradle 4a into the bore 29 of the scan gantry 2 at a fixed rotational position of the rotating section 27 with an X-ray focus of the X-ray tube 20 lying directly above or below. The scout imaging thus carries out registration of the positions of the cradle 4a and of the subject 6, and provides a scout image for the subject 6. Upon completion of the scout imaging, a monitor in the display device 32 displays a scan condition specifying window.

Figure 6:
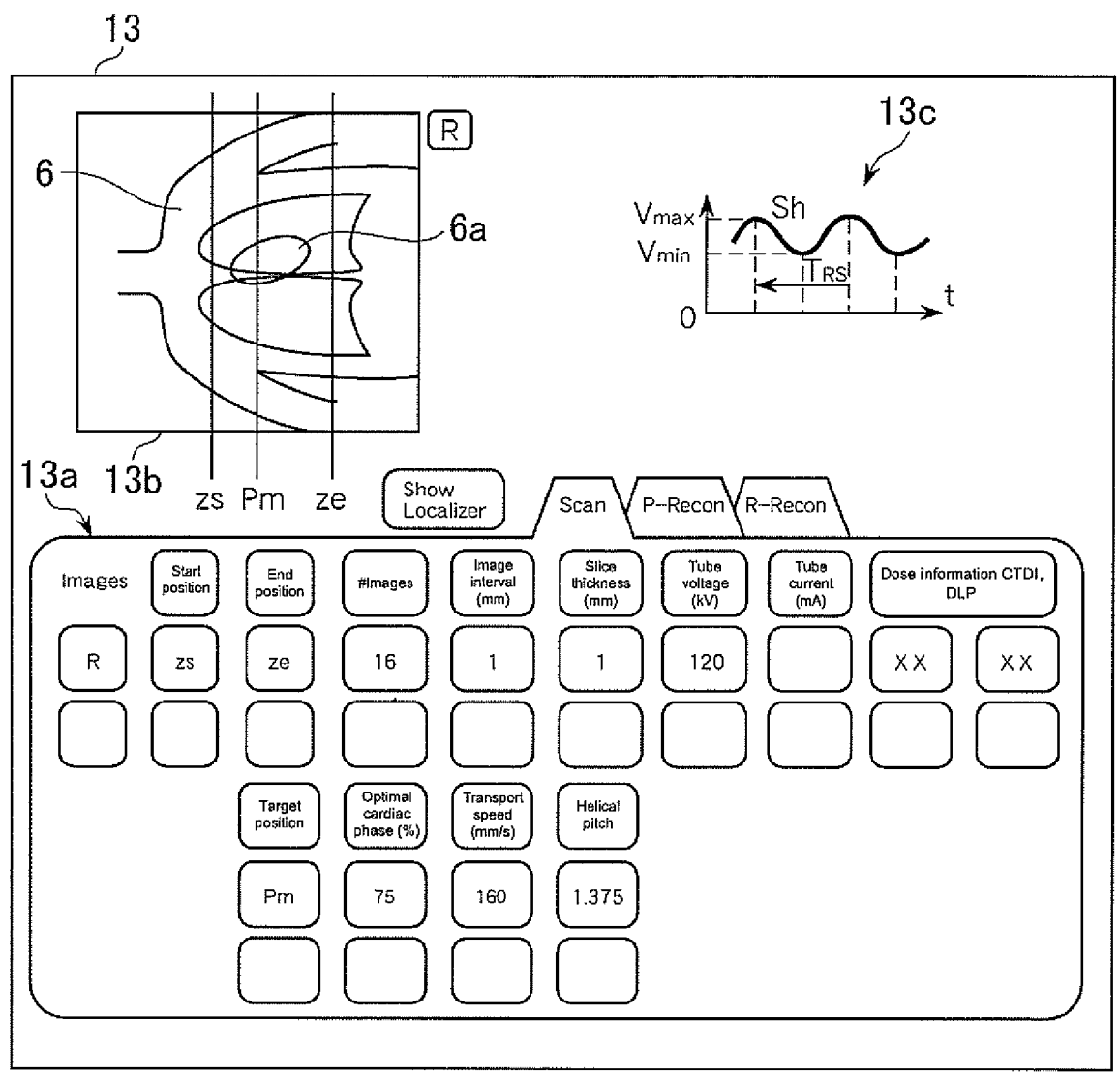
FIG. 6 is a diagram showing an exemplary scan condition specifying window.

FIG. 6 shows an example of the scan condition specifying window. As shown, the scan condition specifying window 13 displays various specification items 13a included in the scan conditions such as, for example, the number of images to be captured, image interval, slice thickness, tube voltage, tube current, optimal cardiac phase, and helical pitch. The scan condition specifying window 13 also displays a scout image 13b of the subject 6 acquired in the scout imaging, and displays electrocardiographic signals Sh being monitored as the electrocardiographic waveform 13c approximately in real time. For an imaging start position zs, an imaging end position ze, a target position Pm, etc., numeric value representing coordinates and symbols are displayed in synchronization with an input operation via GUI.

The operator uses the GUI via the input device 31 to input an imaging start position zs and an imaging end position ze in the z-direction on the scout image 13b. Thus, a range from the input imaging start position zs to the imaging end position ze is defined as imaging range (S102).

The operator also inputs a certain cardiac phase desired to be set as optimal cardiac phase Tgph on the scan condition specifying window 13. The optimal cardiac phase setting section 30b sets the input cardiac phase as optimal cardiac phase Tgph (S103). It should be noted that the optimal cardiac phase Tgph may be set as, instead of a phase itself, a cardiac phase represented by an elapsed time from an R peak in the electrocardiographic waveform, for example. Here, a cardiac phase at 75% is set as optimal cardiac phase Tgph, for example.

Moreover, the operator inputs, on the scout image 13b via GUI, a certain position desired to be defined as target position Pm in the z-direction of the subject 6 that is to be scanned when the cardiac phase of the subject 6 is at the set optimal cardiac phase Tgph. The target position defining section 30c defines the input position as target position Pm (S104). Here, a position of a coronary artery in a heart that is referred to as right coronary artery #2 is defined as target position Pm, for example.

Figure 7:
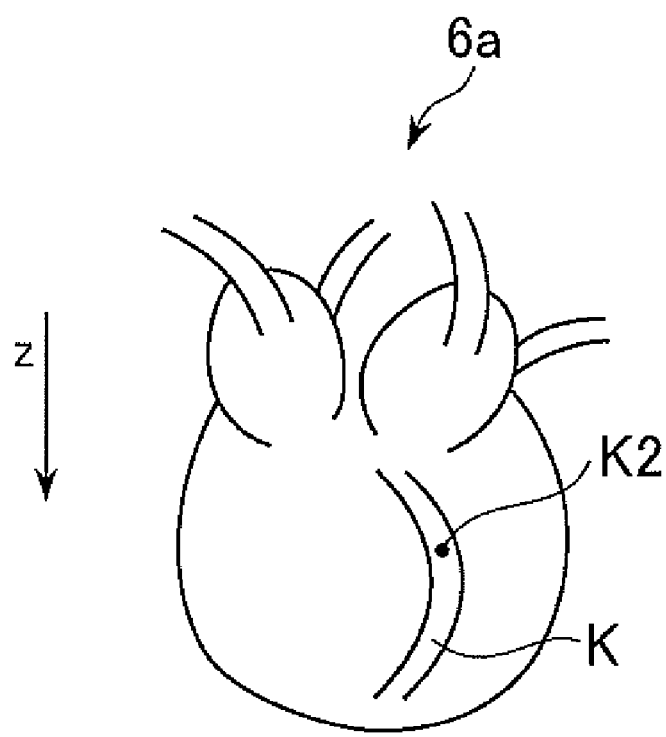
FIG. 7 is a diagram roughly showing an exemplary position of a coronary artery in a heart.

FIG. 7 is a pictorial view roughly showing an exemplary position of a right coronary artery #2 K2 that is a coronary artery K of a heart 6a. The coronary arteries are in an area that exhibits relatively great variation due to cardiac motion and is one of the positions suitable as target position Pm.

Next, the scan control section 30a outputs a control signal to several sections to perform an injection test. The injection test is performed for the purpose of measuring a time from injection of a contrast agent into the subject 6 to arrival of the contrast agent at the imaged area, or confirming whether the contrast injector 8 is controlled as scheduled. For example, the scan control section 30*a* outputs a control signal to the scan gantry 2 and contrast injector 8 to scan the subject 6 for imaging with a low X-ray dose and at a high speed at a position of the rotating section 27 fixed at the scan start position Ps in the z-direction, that is, in a positional relationship such that one end of the scan width of the rotating section 27 coincides with the imaging start position zs, while injecting the contrast agent into the subject 6, whereby a contrast delivery time Tz is measured (S105).

Upon completion of the test injection, the cardiac motion identifying section 30*h* in the central processing apparatus 30 calculates an average cardiac cycle Th by averaging about three to five consecutive cardiac cycles Trs from the latest, based on the electrocardiographic signals Sh sent from the cardiac motion detector 5 (S106).

Next, the transport-starting-cardiac-phase calculating section 30*d* calculates a transport-starting cardiac phase Stph according to EQ. (1) using the average cardiac cycle Th calculated at Step S6, scan start position Ps determined based on the imaging range defined at Step S102, transport speed Vt of the cradle 4*a* determined based on the rotation speed of the rotating section 27 and helical pitch, and previously measured approach-run time Tr for the cradle 4 (S107).

Moreover, the transport-holding-time calculating section 30*e* calculates a transport holding time Tw according to EQ. (2) using the approach-run time Tr for the cradle 4 and contrast delivery time Tz (S108).

The scan control section 30*a* outputs a control signal to the scan gantry 2 and imaging table 4 to rotate the rotating section 27 at a given rotation speed, and to move the cradle 4*a* to a given position such that a position to be scanned in the subject 6 coincides with the scan start position Ps determined based on the imaging range defined as described above after the approach run of the cradle 4*a*.

Thereafter, the scan control section 30*a* controls the contrast injector 8 to inject a contrast agent into the subject 6 (S109), and waits until at least the transport holding time Tw has passed.

The scan control section 30*a* calculates, when starting transport of the cradle 4*a* after the transport holding time Tw has passed from the start of injection of the contrast agent, a difference between the average cardiac cycle Th calculated at Step S6 and the latest cardiac cycle based on the latest cardiac motion identified by the cardiac motion identifying section 30*h*, and checks whether the difference is less than a given period of time, for example, a given time $\Delta$te corresponding to 20% of the average cardiac cycle Th (S110). If the difference is not less than the time $\Delta$te, some anomaly such as arrhythmia is assumed to occur in the cardiac cycle, and the process goes back to Step S110, rather than goes to a next step. On the other hand, if the difference is less than the given time $\Delta$te, a check is made as to whether the latest cardiac phase based on the latest cardiac motion identified by the cardiac motion identifying section 30*h* coincides with the calculated transport-starting cardiac phase Stph (S111). If the latest cardiac phase coincides with the transport-starting cardiac phase Stph, the scan control section 30*a* outputs a control signal to the imaging table 4 to start movement of the cradle 4*a* (S112). On the other hand, if the latest cardiac phase does not coincide with the transport-starting cardiac phase Stph, the process goes back to Step S110. That is, while an anomaly is being observed in a cardiac cycle, the cradle 4*a* is kept from starting an approach run, and is left to wait.

After the approach run of the cradle 4*a* has been completed and the transport speed V has reached a constant speed Vt, the cradle 4*a* has been moved to a position at which the scanned position in the subject 6 coincides with the scan start position Ps, and then, the scan control section 30*a* outputs a control signal to the X-ray controller 25 and data collecting section 24 to generate X-rays at the X-ray tube 20 and cause the X-ray detecting section 23 to detect X-rays passing through the subject 6, thus starting a helical scan, that is, collection of projection data (S113). In the helical scan, the imaging range from the imaging start position zs to the imaging end position ze is scanned over a period of time Ts to collect projection data. During the helical scan, when the cardiac phase of the subject 6 is at the optimal cardiac phase Tgph, the center of the scan width of the rotating section 27 in the z-direction passes through the target position Pm in the subject 6 as calculated if no anomaly such as arrhythmia or the like occurs in the cardiac cycle.

It should be noted that while all collected projection data may be used in image reconstruction, only projection data corresponding to a time zone Tc within the period of time Ts may be extracted for image reconstruction, in which zone the heart 6*a* of the subject 6 is scanned, and a time $\Delta$T1 from a scan start time tss to a time tcs immediately before the scan on the heart 6*a* and a time $\Delta$T2 from a time tce immediately after the scan on the heart 6*a* to a scan end time tse are excluded from the time Ts, for example.

The scan control section 30*a* calculates, during the helical scan, a difference between the average cardiac cycle Th calculated before the helical scan and the latest cardiac cycle based on the latest cardiac motion identified during the helical scan, and checks whether the difference is less than a given period of time, for example, a given time $\Delta$te corresponding to 20% of the average cardiac cycle Th (S114). For example, in a case that a next electrocardiographic gating signal is observed before a lapse of time corresponding to 80% of the average cardiac cycle after the immediately preceding electrocardiographic gating signal synchronous with a heartbeat has been observed, or in a case that no next electrocardiographic gating signal is observed after a lapse of time corresponding to 120% of the average cardiac cycle after the immediately preceding electrocardiographic gating signal has been observed, some anomaly may be assumed to occur in the cardiac cycle. If the difference is not less than the given time $\Delta$te, some anomaly is assumed to occur in the cardiac cycle, and X-ray generation by the X-ray tube 20 is aborted midway through the helical scan, warning is generated using a lamp, a voice, an indicator or the like, and the helical scan is forcefully terminated. The scan control section 30*a* then transports the cradle 4*a* to a given position to allow a second helical scan, and prepares for the second helical scan in synchronization with termination of the preceding helical scan (S115). At that time, instead of moving the cradle 4*a* back to the initial position at one end of the imaging range in the body axis direction of the subject 6, the scan control section 30*a* moves the cradle 4*a* to a given position at the other end of the imaging range to perform the second scan with a reversed direction of transport of the cradle 4*a*. That is, the second helical scan is performed with reversed start and end points in a helical scan.

On the other hand, at Step S13, if the difference is less than the given time $\Delta$te, the scan control section 30*a* checks whether any data to be collected is left (S116), and if no more projection data to be collected is decided to be present, the scan control section 30*a* terminates the scan processing, and the image reconstructing section 30*f* then applies interpolation processing using the collected projection data to calculate projection data required for each slice and reconstructs a tomographic image for each slice (S117). The resulting tomographic image or a three-dimensional image, an MPR image or the like based on such tomographic images is displayed on a monitor in the display device 32 (S118). If data to be collected is decided to be left, the process goes back to Step S114 to continue collection of projection data.

According to the X-ray CT apparatus in such an embodiment, once an optimal cardiac phase Tgph has been set by the optimal cardiac phase setting section 30b, and a target position Pm in the subject 6 has been defined by the target position defining section 30c, the transport-starting-cardiac-phase calculating section 30d calculates a transport-starting cardiac phase Stph such that the target position Pm is scanned at the optimal cardiac phase Tgph, using the cardiac cycle Th of the subject 6, scan start position Ps in the subject 6, transport speed V of the imaging table 4, and approach-run time Tr for the imaging table 4, and the scan control section 30a starts transport of the imaging table 4 to perform a helical scan on the subject 6 when the cardiac phase of the subject 6 coincides with the transport-starting cardiac phase Stph; therefore, imaging can be made on a region to be imaged in the subject 6 at a high speed and with a low X-ray dose such that a desired portion in the subject 6, for example, a portion having significant variation due to heartbeats, can be scanned at a desired cardiac phase, for example, at a phase at which the variation due to heartbeats is slowest, and thus, it is possible to image the heart 6a of the subject 6 with high image quality while reducing stress on the subject 6.

Moreover, according to the present embodiment, the scan control section 30a calculates, during the helical scan, a difference between an average cardiac cycle Th calculated before the helical scan and the latest cardiac cycle identified during the helical scan, and when the difference is less than a given time Ate, the scan control section 30a assumes that some anomaly has occurred in the cardiac cycle, and aborts X-ray generation, generates warning, and forcefully terminates the helical scan; therefore, even when imaging has failed, the failure can be notified to the operator or the like, and exposure of the subject 6 can be minimized.

Furthermore, the scan control section 30a thereafter transports the cradle 4a to a given position to allow a second helical scan and prepares for the second helical scan in synchronization with termination of the helical scan; therefore, even when imaging has failed, the process immediately proceeds with preparation for next imaging, thus allowing time-efficient imaging. At that time, instead of moving the cradle 4a back to the initial position at one end of an imaging range in the body axis direction of the subject 6, the scan control section 30a moves the cradle 4a to a given position at the other end of the imaging range to perform the second helical scan with a reversed direction of transport of the cradle 4a, thus allowing more time-efficient imaging.

An X-ray CT apparatus in accordance with another embodiment of the present invention will be described.

Figure 8:
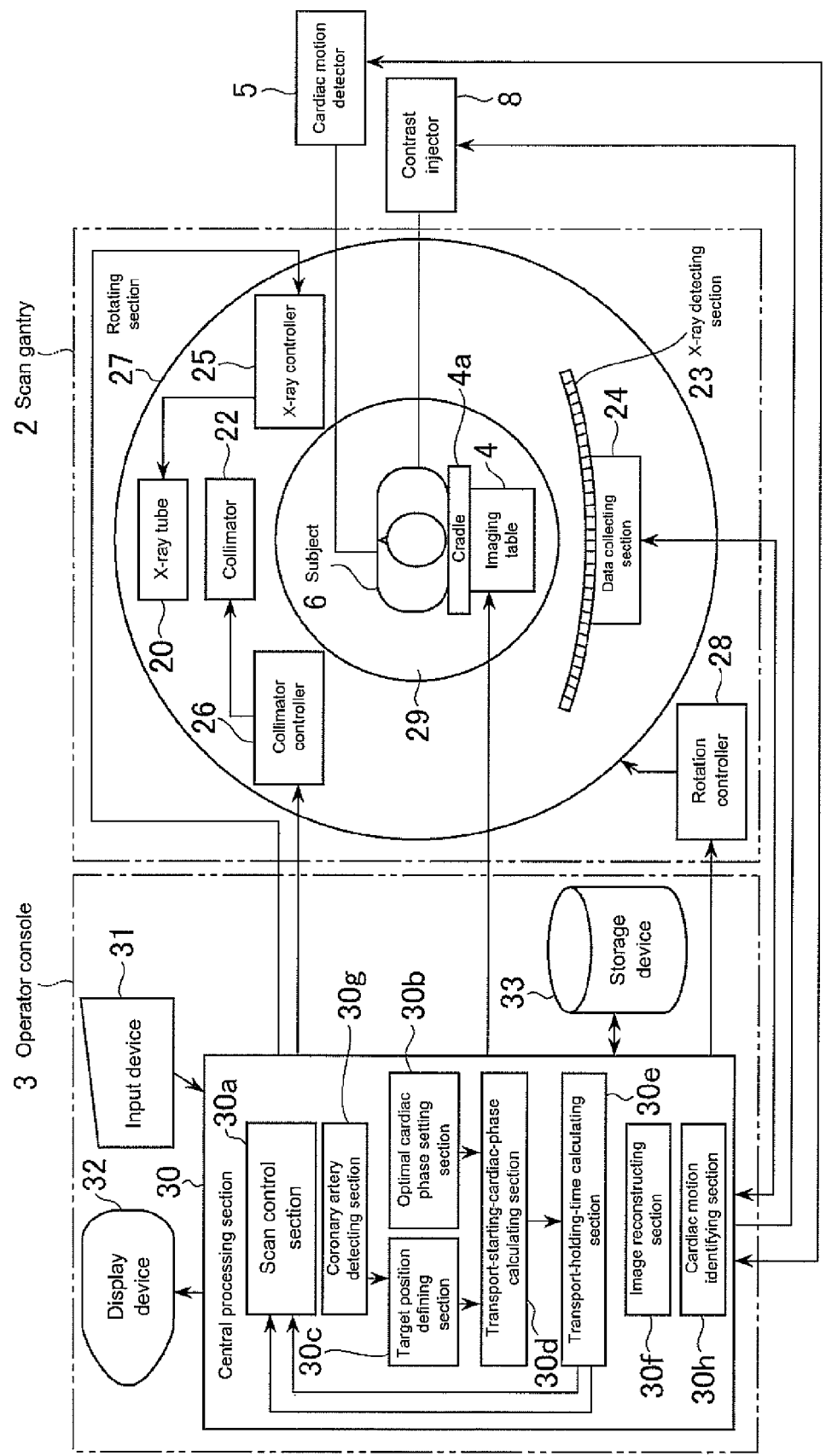
FIG. 8 is a diagram showing a configuration of an X-ray CT apparatus in accordance with another embodiment of the present invention.

FIG. 8 is a block diagram showing an overall configuration of an X-ray CT apparatus 1 of the present embodiment. The X-ray CT apparatus 1 in the present embodiment basically has a similar configuration to that in the first embodiment except differences as follows: While in the first embodiment, the target position defining section 30c defines a given position input by the operator on an image of the subject 6 as target position Pm, in the present embodiment, the central processing apparatus 30 further comprises a coronary artery detecting section 30g for analyzing an image of the subject 6 acquired in scout imaging or in a preliminary helical scan to detect an image representing a coronary artery, for example, a right coronary artery #2, in the subject 6, and the target position defining section 30c defines the position of the image representing the detected right coronary artery #2 as target position.

The coronary artery detecting section 30g detects an image representing a coronary artery on, for example, a scout image of the subject 6 using CT value-based edge detection, template matching or the like, and thereafter, it detects a right coronary artery #2 as an image at a position that divides the image of the coronary artery in a given ratio, or as a presumptive portion in the image that has the most significant variation over a plurality of images of the subject 6 acquired in a plurality of number of times of scout imaging, preliminary helical scanning or cine scanning with a low X-ray dose, or simply as an image at the central position in the z-direction in a predefined imaging range.

Figure 9:
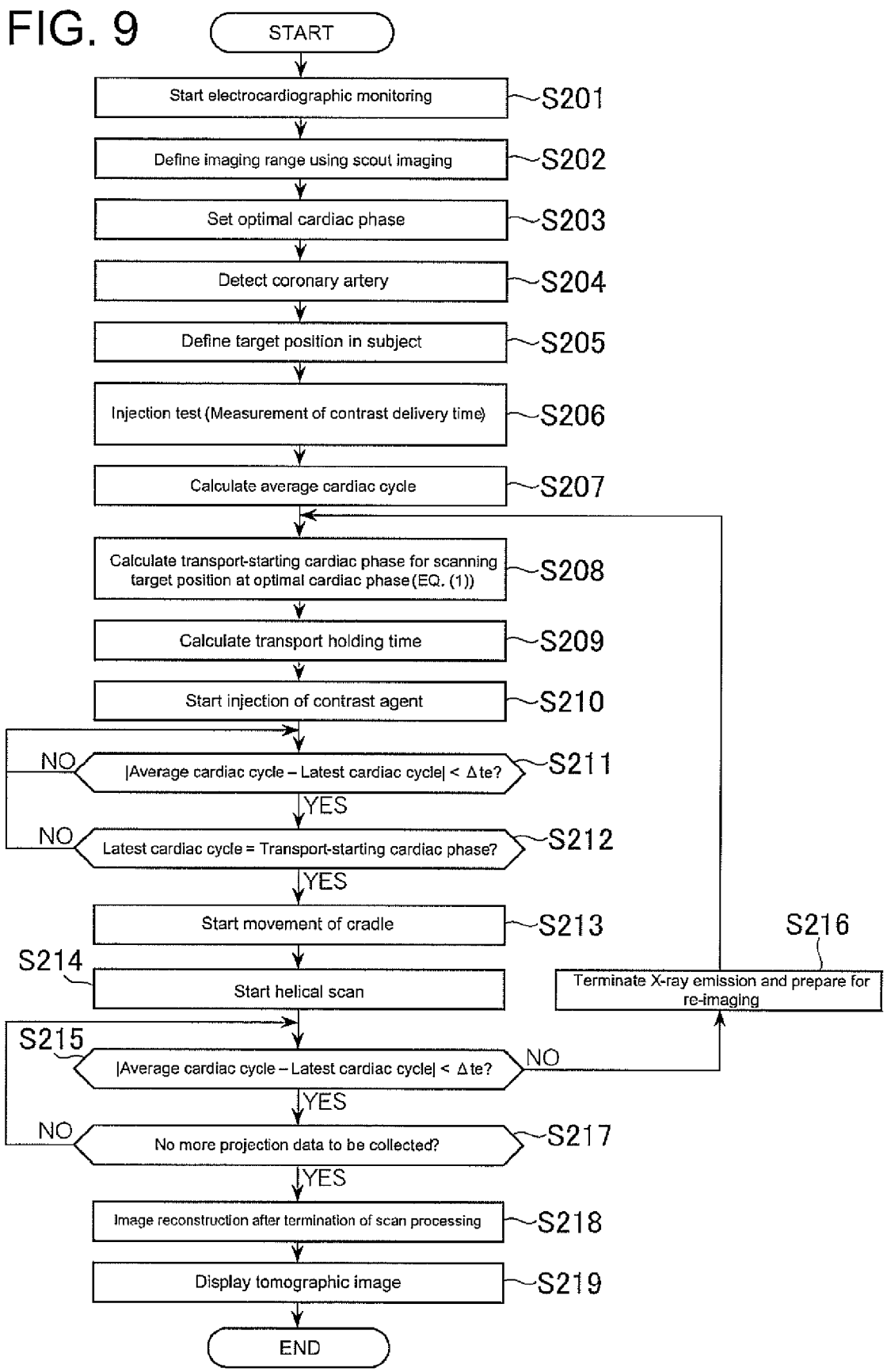
FIG. 9 is a flow chart showing an X-ray CT imaging method using the X-ray CT apparatus in accordance with another embodiment of the present invention.

FIG. 9 is a flow chart showing an X-ray CT imaging method using the X-ray CT apparatus in accordance with the present embodiment. Steps S201-S203 correspond to Steps S101-S103 in the first embodiment, and Steps S205-S219 correspond to Steps S104-S118 in the first embodiment. In the present embodiment, at Step S204, the coronary artery detecting section 30g performs image analysis on an image of the subject 6 acquired in scout imaging or the like to detect an image of a right coronary artery #2, and defines the position of the image as target position Pm. That is, in the present embodiment, rather than the operator inputs a certain position, a right coronary artery #2 is detected and its position is automatically defined as target position Pm. Since there may be a case that the target position Pm is defined at a position somewhat offset from the true right coronary artery #2 according to a result of image analysis, the target position defining section 30g is desirably provided with a function of allowing the operator to later adjust the target position Pm.

According to the X-ray CT apparatus in such an embodiment, the coronary artery detecting section 30g automatically detects an image of a right coronary artery #2, and defines the position of the image as target position Pm; therefore, scan conditions can be automatically specified such that a position having the most significant variation due to cardiac motion can be scanned at an optimal cardiac phase Tgph, that is, at a cardiac phase of 75%, for example, at which variation due to heartbeats is slowest, and scan conditions that the operator ordinarily desires can be specified without tedious input operations by the operator.

It should be noted that while description has been made on a case in which the helical pitch in performing a helical scan is one or more in the aforementioned embodiments, that case is taken to illustrate an example possibly well-balanced among image quality of a tomographic image, subject exposure dose, time efficiency, and the like, taking account of the width of an X-ray detecting section in the slice direction in multi-slice CT apparatuses that are common at the time of filing of the present application. Therefore, when the width of the X-ray detecting section in the slice direction is expanded in the future or when image quality of a tomographic image is to be further improved, the helical pitch may be less than one, or may be about 0.7 or about 0.5, for example, according to such conditions.

Moreover, while description has been made on a case of contrast imaging in which the contrast injector 8 is used to inject a contrast agent into the subject 6 in the aforementioned embodiments, it will be easily recognized that the embodiments of the present invention may be applied to ordinary imaging without a contrast agent.

The aforementioned embodiments are provided merely by way of example of the best mode for carrying out the present invention, and the present invention is not limited to these embodiments. That is, all variations, additions and combinations are possible in the present invention insofar as they are not deviated from the spirit of the present invention.

In addition, a program that causes a computer to serve as the scan control device, cardiac motion identifying device, optimal cardiac phase setting device, target position defining device, transport-starting-cardiac-phase calculating device, transport-holding-time calculating device, image reconstructing device, and coronary artery detecting device in the present invention may constitute an exemplary embodiment of the present invention. It should be noted that such a program may be supplied by downloading or distributing it via a network such as the Internet, or by recording it in a computer-readable recording medium.

The invention claimed is:

1. An X-ray CT apparatus comprising:
   an X-ray data collecting system comprising an X-ray generating section configured to generate X-rays and an X-ray detecting section comprising a multiplicity of X-ray detector elements two-dimensionally arranged, facing each other across a cavity and provided rotatably around a given axis;
   an imaging table configured to carry a subject placed thereon through said cavity along the given axis;
   a scan control device configured to control said X-ray data collecting system and said imaging table to perform a first helical scan on the subject to collect projection data;
   an image reconstructing device configured to perform image reconstruction processing based on the collected projection data to produce a tomographic image of the subject;
   a cardiac motion identifying device configured to identify cardiac motion of the subject;
   an optimal cardiac phase setting device configured to set an optimal cardiac phase for the subject;
   a target position defining device configured to determine a target position to be scanned in a direction along the given axis of the subject when a cardiac phase for the subject is at the optimal cardiac phase; and
   a transport-starting-cardiac-phase calculating device configured to calculate a transport-starting cardiac phase corresponding to a time at which transport of said imaging table is to be started such that the target position is scanned at the optimal cardiac phase, using a cardiac cycle of the subject determined based on the identified cardiac motion, a scan start position in the subject, a transport speed of said imaging table, and an approach-run time for said imaging table, the transport-starting cardiac phase calculated according to the following equation:

$$Stph = Tgph - ((((Pm - Ps)/Vt + Tr)/Th) \times 100),$$

where Stph denotes the transport-starting cardiac phase, Tgph denotes the optimal cardiac phase, Pm denotes the target position, Ps denotes the scan start position, Vt denotes the transport speed, Tr denotes the approach-run time, and Th denotes the cardiac cycle, and wherein said scan control device is further configured to control said imaging table to start transport of said imaging table when the cardiac phase of the subject determined based on the identified cardiac motion coincides with the calculated transport-starting cardiac phase.

2. The X-ray CT apparatus as defined by claim 1, wherein: said scan control device is configured to control said X-ray data collecting system to abort X-ray generation by said X-ray generating section midway through the first helical scan when a difference between the cardiac cycle based on cardiac motion identified by said cardiac motion identifying device before the first helical scan and the cardiac cycle based on cardiac motion identified by said cardiac motion identifying device during the first helical scan is one of equal to and greater than a given period of time.

3. The X-ray CT apparatus as defined by claim 1, wherein: said scan control device is configured to generate a warning when the difference between the cardiac cycle based on cardiac motion identified by said cardiac motion identifying device before the first helical scan and the cardiac cycle based on cardiac motion identified by said cardiac motion identifying device during the first helical scan is one of equal to and greater than a given period of time.

4. The X-ray CT apparatus as defined by claim 1, wherein: said scan control device is configured to control said X-ray data collecting system and said imaging table to perform a second helical scan in synchronization with termination of the first helical scan when the difference between the cardiac cycle based on cardiac motion identified by said cardiac motion identifying device before the first helical scan and the cardiac cycle based on cardiac motion identified by said cardiac motion identifying device during the first helical scan is one of equal to and greater than a given period of time.

5. The X-ray CT apparatus as defined by claim 4, wherein: said scan control device is configured to control said X-ray data collecting system to perform the second helical scan with a reversed direction of transport of said imaging table.

6. The X-ray CT apparatus as defined by claim 1, wherein: said scan control device is configured to control said X-ray data collecting system and said imaging table to perform the first helical scan with a helical pitch of one or more.

7. The X-ray CT apparatus as defined by claim 1, wherein: said scan control device is configured to control said X-ray data collecting system and said imaging table to perform the first helical scan at a cycle of rotation of said X-ray data collecting system of 0.4 seconds or less.

8. An X-ray CT apparatus comprising:
   an X-ray data collecting system comprising an X-ray generating section configured to generate X-rays and an X-ray detecting section comprising a multiplicity of X-ray detector elements two-dimensionally arranged, facing each other across a cavity and provided rotatably around a given axis;
   an imaging table configured to carry a subject placed thereon through said cavity along the given axis;
   a scan control device configured to control said X-ray data collecting system and said imaging table to perform a first helical scan on the subject to collect projection data;
   an image reconstructing device configured to perform image reconstruction processing based on the collected projection data to produce a tomographic image of the subject;
   a cardiac motion identifying device configured to identify cardiac motion of the Subject;
   an optimal cardiac phase setting device configured to set an optimal cardiac phase for the subject;
   a target position defining device configured to determine a target position to be scanned in a direction along the given axis of the subject when a cardiac phase for the subject is at the optimal cardiac phase;
   a transport-staffing-cardiac-phase calculating device configured to calculate a transport-starting cardiac phase corresponding to a time at which transport of said imaging table is to be started such that the target position is scanned at the optimal cardiac phase, using a cardiac cycle of the subject determined based on the identified cardiac motion, a scan staff position in the subject, a transport speed of said imaging table, and an approach-run time for said imaging table, wherein said scan control device is further configured to control said imaging table to start transport of said imaging table when the cardiac phase of the subject determined based on the identified cardiac motion coincides with the calculated transport-starting cardiac phase;

a contrast injector device configured to inject a contrast agent into the subject; and a transport-holding-time calculating device configured to calculate a transport holding time that should be kept from the start of injection of the contrast agent to the start of transport of said imaging table, using an approach-run time for said imaging table and a contrast delivery time representing a time required from injection of the contrast agent to arrival of said contrast agent at an imaged area, the transport holding time calculated according to the following equation:

$Tw=Tz-Tr;$ where Tw denotes the transport holding time, Tz denotes the contrast delivery time, and Tr denotes the approach-run time, and wherein said scan control device is configured to control said contrast injector device to inject the contrast agent into the subject, said scan control device is further configured to control said imaging table to start transport of said imaging table after at least the transport holding time has passed.

9. The X-ray CT apparatus as defined by claim 1, wherein: said optimal cardiac phase setting device is configured to set the optimal cardiac phase within 70-80%, where a phase covering a range from a peak of a first R-wave to a peak of a second R-wave subsequent to the first R-wave in a heartbeat waveform is represented as 0-100%.

10. The X-ray CT apparatus as defined by claim 1, wherein: said scan control device is configured to control said X-ray data collecting system and said imaging table to perform scout imaging on the subject before the first helical scan, and said target position defining device is configured to determine the target position on an image of the subject acquired in the scout imaging.

11. The X-ray CT apparatus as defined by claim 1, wherein: said scan control device is configured to control said X-ray data collecting system and said imaging table to perform a preliminary helical scan on the subject before the first helical scan, and said target position defining device is configured to determine the target position on an image of the subject acquired in the preliminary helical scan.

12. The X-ray CT apparatus as defined by claim 10, further comprising:

a coronary artery detecting device configured to detect an image representing a coronary artery of the subject by analyzing an image of the subject, wherein said target position defining device is configured to determine the target position at the position of the image representing the detected coronary artery.

13. The X-ray CT apparatus as defined by claim 11, further comprising:

a coronary artery detecting device for detecting an image representing a coronary artery of the subject by analyzing an image of the subject, wherein said target position defining device is configured to determine the target position at the position of the image representing the detected coronary artery.

14. The X-ray CT apparatus as defined by claim 12, wherein: the coronary artery is a right coronary artery #2.

15. The X-ray CT apparatus as defined by claim 13, wherein: the coronary artery is a right coronary artery #2.

16. The X-ray CT apparatus as defined by claim 1, wherein: said cardiac motion identifying device is configured to identify cardiac motion based on signals acquired by a cardiograph.

17. The X-ray CT apparatus as defined by claim 1, wherein: said cardiac motion identifying device is configured to identify cardiac motion based on signals acquired by a pulsemeter.

* * * * *